United States Patent
Zhang et al.

(10) Patent No.: US 9,814,424 B2
(45) Date of Patent: Nov. 14, 2017

(54) CHRONIC OBSTRUCTIVE PULMONARY DISEASE DRUG TITRATION AND MANAGEMENT

(71) Applicant: Cardiac Pacemakers, Inc., St. Paul, MN (US)

(72) Inventors: Yi Zhang, Plymouth, MN (US); Pramodsingh Hirasingh Thakur, Woodbury, MN (US); Kenneth C. Beck, Liberty, UT (US); Bryan Allen Clark, Forest Lake, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 407 days.

(21) Appl. No.: 14/540,623

(22) Filed: Nov. 13, 2014

(65) Prior Publication Data
US 2015/0157260 A1    Jun. 11, 2015

Related U.S. Application Data
(60) Provisional application No. 61/912,912, filed on Dec. 6, 2013.

(51) Int. Cl.
*A61B 5/0452* (2006.01)
*A61B 5/053* (2006.01)
(Continued)

(52) U.S. Cl.
CPC .......... *A61B 5/4848* (2013.01); *A61B 5/0452* (2013.01); *A61B 5/053* (2013.01);
(Continued)

(58) Field of Classification Search
CPC ..... A61B 5/021; A61B 5/0245; A61B 5/0452; A61B 5/053; A61B 5/08; A61B 5/0809;
(Continued)

(56) References Cited

U.S. PATENT DOCUMENTS 6,076,015 A      6/2000  Hartley et al.
7,171,258 B2 *  1/2007  Goode ................... A61B 5/053
                                                                600/509

(Continued)

FOREIGN PATENT DOCUMENTS

| CN | 105814569 A | 7/2016 |
|----|----|----|
| WO | WO-2015084557 A1 | 6/2015 |

OTHER PUBLICATIONS

Chiappini, B., et al., "Risk of atrial fibrillation with high-dose corticosteroids", Expert Opin Drug Saf, 2006. 5(6), (2006), 811-814.

(Continued)

*Primary Examiner* — Navin Natnithithadha
(74) *Attorney, Agent, or Firm* — Schwegman Lundberg & Woessner, P.A.

(57) ABSTRACT

A system may include a port, at least one sensing circuit, and at least one processor. The port is configured to receive an indication of dosing of medication to treat a pulmonary condition of a heart failure (HF) subject and the at least one sensing circuit configured to sense at least one physiological signal, wherein the physiological signal includes physiological information of the HF subject. The at least one processor includes a parameter module configured to extract values of at least one physiological parameter indicative of health status of the HF subject, and a trending module configured to trend extracted values of the at least one physiological parameter and detect an effect of the dosing of the medication on the HF subject using the trending of the extracted values of the at least one physiological parameter.

18 Claims, 3 Drawing Sheets

(51) Int. Cl.

| | |
|---|---|
| *A61B 5/08* | (2006.01) |
| *A61B 5/091* | (2006.01) |
| *A61B 7/04* | (2006.01) |
| *A61M 5/172* | (2006.01) |
| *A61N 1/365* | (2006.01) |
| *A61B 5/021* | (2006.01) |
| *A61B 5/00* | (2006.01) |
| *A61B 5/1455* | (2006.01) |
| *G06F 19/00* | (2011.01) |
| *A61B 5/145* | (2006.01) |
| *A61B 5/0245* | (2006.01) |

(52) U.S. Cl.
CPC ............... *A61B 5/08* (2013.01); *A61B 5/082* (2013.01); *A61B 5/0809* (2013.01); *A61B 5/0816* (2013.01); *A61B 5/091* (2013.01); *A61B 5/14542* (2013.01); *A61B 5/14552* (2013.01); *A61B 5/7275* (2013.01); *A61B 7/04* (2013.01); *A61M 5/172* (2013.01); *A61N 1/365* (2013.01); *G06F 19/34* (2013.01); *G06F 19/3462* (2013.01); *A61B 5/021* (2013.01); *A61B 5/0245* (2013.01)

(58) Field of Classification Search
CPC ....... A61B 5/0816; A61B 5/082; A61B 5/091; A61B 5/14542; A61B 5/14552; A61B 5/4848; A61B 5/7275; A61B 7/04; A61M 5/172
USPC ......... 600/481, 483, 508, 509, 513, 529, 537
See application file for complete search history.

(56) References Cited

U.S. PATENT DOCUMENTS

| | | | |
|---|---|---|---|
| 7,433,853 B2 | 10/2008 | Brockway et al. | |
| 7,517,328 B2 | 4/2009 | Hoffmann | |
| 7,662,105 B2* | 2/2010 | Hatlestad | A61B 5/0809 600/529 |
| 7,731,663 B2* | 6/2010 | Averina | A61B 5/0816 600/483 |
| 7,826,891 B2* | 11/2010 | Goode | A61B 5/053 600/509 |
| 7,927,284 B2* | 4/2011 | Dalal | A61B 5/02028 600/481 |
| 8,079,968 B2 | 12/2011 | Hoffmann | |
| 8,145,590 B2 | 3/2012 | Brockway et al. | |
| 8,340,747 B2* | 12/2012 | Goode, Jr. | A61B 5/053 600/509 |
| 8,372,012 B2* | 2/2013 | Averina | A61B 5/0816 600/483 |
| 8,496,596 B2* | 7/2013 | Hatlestad | A61B 5/0809 600/484 |
| 8,594,789 B2* | 11/2013 | Goode, Jr. | A61B 5/053 600/509 |
| 8,998,821 B2* | 4/2015 | Hatlestad | A61B 5/0809 600/529 |
| 9,173,575 B2* | 11/2015 | Woodford | A61B 5/0205 |
| 2004/0267142 A1* | 12/2004 | Paul | A61B 5/053 600/509 |
| 2005/0137626 A1 | 6/2005 | Pastore et al. | |
| 2007/0049835 A1* | 3/2007 | Goode | A61B 5/053 600/509 |
| 2007/0065363 A1* | 3/2007 | Dalal | A61B 5/02028 424/9.1 |
| 2007/0073169 A1* | 3/2007 | Averina | A61B 5/0816 600/483 |
| 2007/0118054 A1* | 5/2007 | Pinhas | A61B 5/1104 600/587 |
| 2007/0135725 A1* | 6/2007 | Hatlestad | A61B 5/0809 600/529 |
| 2008/0294209 A1 | 11/2008 | Thompson et al. | |
| 2009/0275848 A1* | 11/2009 | Brockway | A61B 5/0205 600/513 |
| 2010/0137730 A1* | 6/2010 | Hatlestad | A61B 5/0809 600/529 |
| 2010/0228133 A1* | 9/2010 | Averina | A61B 5/0816 600/484 |
| 2011/0009767 A1* | 1/2011 | Goode | A61B 5/053 600/547 |
| 2011/0230771 A1* | 9/2011 | Koh | A61B 5/01 600/485 |
| 2012/0041279 A1* | 2/2012 | Freeman | A61B 5/0205 600/301 |
| 2012/0130697 A1* | 5/2012 | Woodford | A61B 5/0205 703/11 |
| 2013/0024176 A2* | 1/2013 | Woodford | A61B 5/0205 703/11 |
| 2013/0102914 A1* | 4/2013 | Goode, Jr. | A61B 5/053 600/526 |
| 2013/0150745 A1* | 6/2013 | Averina | C07C 17/361 600/529 |
| 2013/0245502 A1* | 9/2013 | Lange | A61B 5/1102 600/595 |
| 2013/0303928 A1* | 11/2013 | Hatlestad | A61B 5/0809 600/529 |
| 2016/0150996 A9* | 6/2016 | Averina | C07C 17/361 600/529 |

OTHER PUBLICATIONS

Clyburn, E. B., et al., "Hypertension induced by drugs and other substances", Semin Nephrol, (1995), 72-86.
Davies, L., et al., "Oral corticosteroids in patients admitted to hospital with exacerbations of chronic obstructive pulmonary disease: a prospective randomnised controlled trial", Lancet, 1999 354(9177), (1999), 456-460.
Decramer, M., et al., "Targeting the COPD exacerbation", Respir Med 102 Suppl 1, (2008), S3-15.
Evensen, A. E., "Management of COPD exacerbations", Am Fam Physician, 2010. 81(5), (2010), 607-613.
Fonarow, G. C., et al., "Temporal trends in clinical characteristics, treatments, and outcomes for heart failure hospitalizations, 2002 to 2004: findings from Acute Decompensated Heart Failure National Registry", Am Heart J, 2007. 153(6):, (2007), 1021-1028.
Greene, M. A., et al., "Clinical and cardiodynamic effects of adrenocortical steroids in congestive heart failure", Circulation, 1960. 21, (1960), 661-671.
McCrory, D. C., et al., "Management of acute exacerbations of COPD: a summary and appraisal of published evidence", Chest, 2001. 119(4), (2001), 1190-1209.
Niewoehner, D. E., et al., "Effect of systemic glucocorticoids on exacerbations of chronic obstructive pulmonary disease", N Engl J Med, 1999. 340(25), Department of Veterans Affairs Cooperative Study Group, (1999), 1941-1947.
Quon, B. S., et al., "Contemporary management of acute exacerbations of COPD: a systematic review and metaanalysis", Chest, 2008. 133(3), (2008), 756-766.
Rabe, K. F., "Global strategy for the diagnosis, management, and prevention of chronic obstructive pulmonary disease: GOLD executive summary", Am J Respir Crit Care Med 176(6):, (2007), 532-555.
Singh, J. M., et al., "Corticosteroid therapy for patients with acute exacerbations of chronic obstructive pulmonary disease: a systematic review", Arch Intern Med 162(22):, (2002), 2527-2536.
Van Der Hooft, C.S., et al., "Corticosteroids and the risk of atrial fibrillation", Arch Intern Med, 2006, 166(9), (2006), 1016-1020.
Walters, J. A., et al., "Systemic corticosteroids for acute exacerbations of chronic obstructive pulmonary disease", Cochrane Database Syst Rev, (2009), CD001288.
Wilkinson, T. M., et al., "Early therapy improves outcomes of exacerbations of chronic obstructive pulmonary disease", Am J Respir Grit Care Med, 2004. 169(12), (2004), 1298-1303.
"International Application Serial No. PCT/US2014/065357, International Preliminary Report on Patentability dated Jun. 16, 2016", 11 pgs.

(56) References Cited

OTHER PUBLICATIONS

"International Application Serial No. PCT/US2014/065357, International Search Report dated Apr. 29, 2015", 4 pgs.
"International Application Serial No. PCT/US2014/065357, Written Opinion dated Apr. 29, 2015", 10 pgs.
Celler, B G, et al., "A Clinical Monitoring and Management System for Residential Aged Care Facilities", Conference Proceedings. Annual International Conference of The Ieee Engineering in Medicine and Biology Society New York, NY, USA, (Aug. 30, 2006), 3301-3304.

* cited by examiner

CHRONIC OBSTRUCTIVE PULMONARY DISEASE DRUG TITRATION AND MANAGEMENT

CLAIM OF PRIORITY

This application claims the benefit of priority under 35 U.S.C. §119(e) of U.S. Provisional Patent Application Ser. No. 61/912,912, filed on Dec. 6, 2013, which is herein incorporated by reference in its entirety.

BACKGROUND

Patients diagnosed with heart failure (HF) may receive medication to treat a pulmonary condition. For example, chronic obstructive pulmonary disease (COPD) is a common comorbidity for HF patients. COPD is a progressive lung disease and includes chronic bronchitis and emphysema. An exacerbation of COPD is a sudden worsening of symptoms (e.g. increase in or onset of cough, wheeze, and sputum changes) that typically lasts from several days to a couple of weeks. Asthma is another pulmonary condition that may be a comorbidity of HF patients. Cortico-steroid therapy is commonly prescribed to treat COPD exacerbations and asthma attacks to help reduce airway obstruction. However, prescribing cortico-steroids for an HF patient is complicated by the fact that cortico-steroids can have negative effects for the HF patient, such as elevation of the risk of developing arrhythmias, and retention of sodium and water that can exacerbate hypertension and congestion for the patient. The present inventors have recognized a need for improved monitoring of treatment of pulmonary conditions for patients with HF.

OVERVIEW

This document discusses systems, devices and methods for improved monitoring of dosing of a patient to treat a pulmonary condition. A system example can include a port, at least one sensing circuit, and at least one processor. The port is configured to receive an indication of dosing of medication to treat a pulmonary condition of a heart failure (HF) subject and the at least one sensing circuit configured to sense at least one physiological signal, wherein the physiological signal includes physiological information of the HF subject. The at least one processor includes a parameter module configured to extract values of at least one physiological parameter indicative of health status of the HF subject, and a trending module configured to trend extracted values of the at least one physiological parameter and detect an effect of the dosing of the medication on the HF subject using the trending of the extracted values of the at least one physiological parameter.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

An ambulatory medical device can be implantable, partially implantable, or wearable and non-implantable, and may include one or more of the features, structures, methods, or combinations thereof described herein. For example, an ambulatory respiration monitor may be implemented to include one or more of the advantageous features or processes described below. It is intended that such a monitor, or other implantable, partially implantable, or wearable device need not include all of the features described herein, but may be implemented to include selected features that provide for unique structures or functionality. Such a device may be implemented to provide a variety of diagnostic functions.

As explained previously herein, HF patients may receive medication to treat a pulmonary condition. For instance, an HF patient may be prescribed cortico-steroids to treat COPD. However, medication such as cortico-steroids can have negative effects for the HF patient. Therefore in some situations it may be desirable to use a relatively low dosage of medication for the HF patient that is still effective to treat the pulmonary condition with minimal adverse side effects. Device-based monitoring of the respiratory and cardiac function of a patient with HF may be useful in determining the effective dosage of medication for the patient.

Figure 1:
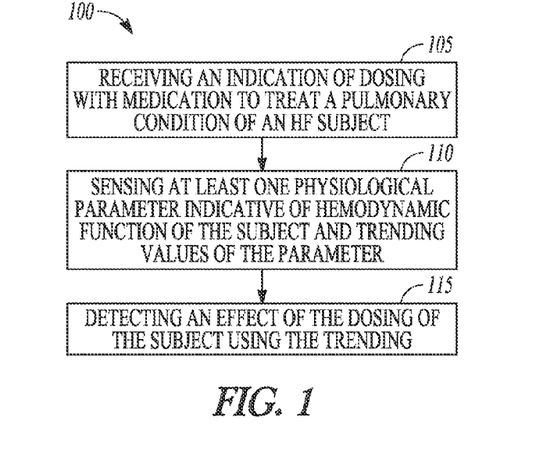
FIG. 1 shows a flow diagram of an example of a method of operating a medical device to monitor effects of dosing of a heart failure subject.

FIG. 1 shows a flow diagram of an example of a method 100 of operating a medical device to monitor effects of dosing of a heart failure (HF) patient or subject. The medical device may be implantable, partially implantable, or wearable. At block 105, an indication of dosing of medication to treat a pulmonary condition of the subject is received into the medical device. The notification may be from a user or the notification may be an automatic notification from a separate device. The automatic notification may be initiated by the user of the separate device or initiated by an electronic medical records system.

At block 110, at least one physiological parameter indicative of health status of the HF subject is sensed using the medical device. Some examples of such a physiological parameter include heart rate, blood pressure, respiration, a measure of heart contractility, thoracic impedance, arrhythmia burden, and at least one heart sound parameter. Arrhythmia burden refers to the amount of time in a given period that the HF subject experiences arrhythmia and can be measured as a percentage of time, a number of arrhythmia events in a specified time period, or an amount of time of arrhythmia in a specified time period. Heart sounds are associated with mechanical cardiac activity. This is in contrast to electrical cardiac activity that is associated with electrical action potentials due to cardiac depolarization. A "heart sound" can include a first heart sound (S1), a second heart sound (S2), a third heart sound (S3), a fourth heart sound (S4), or any components thereof, such as the aortic component of S2 (A2), the pulmonary component of S2 (P2), or other broadband sounds or vibrations associated with mechanical activity of the heart, such as valve closures or fluid movement (e.g., a heart murmur, etc.). Heart sounds can also include one or more broadband chest sounds, such as may result from one or more of mitral regurgitation, left ventricle dilation, etc. The values of the physiological parameter or parameters can be trended with time.

At block 115, an effect of the dosing of the medication on the HF subject is detected using the trending of values of the physiological parameter or parameters. The effect may be detected when the parameter value or values exceeds a specified detection threshold or falls outside of specified range of parameter values. The indication of the effect can be provided to at least one of a user or process.

Figure 2:
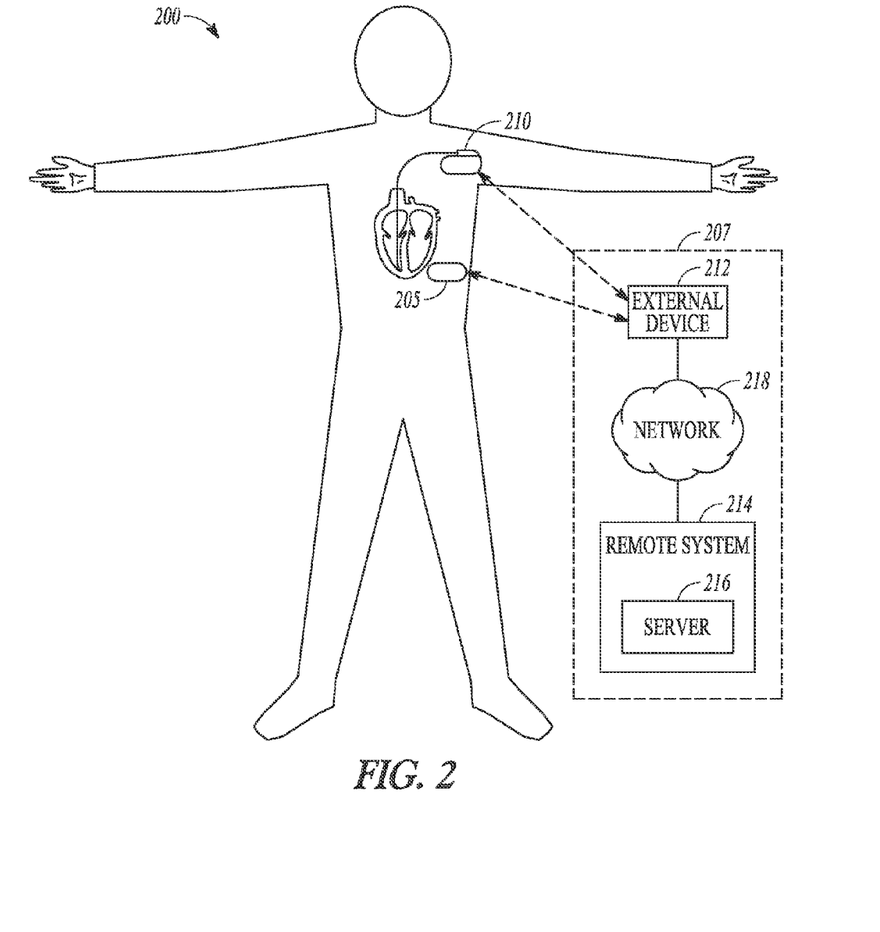
FIG. 2 shows portions of an example of a medical device system for monitoring effects of dosing of a heart failure subject.

FIG. 2 shows an example of a medical device system 200. The system 200 includes an ambulatory device for monitoring effects of dosing of an HF subject. The ambulatory device can be a wearable device 205, such as a patch or vest that monitors one or more physiological parameters of the subject for example. The wearable device 205 may be incorporated into an article of clothing or may be adherable to the subject's skin. The ambulatory device can be an implantable device 210, such as a pacemaker or implantable cardioverter/defibrillator (ICD, e.g., transvenous ICD or subcutaneous ICD) that provides electrical therapy to the HF subject. In certain examples, the implantable device 210 can include a drug reservoir to provide a drug therapy to the HF patient, or the implantable device 210 can be a monitoring device used only for diagnostic purposes. In some examples, the medical device system 200 includes both an implantable device 210 and a wearable device 205. The combination may be desirable based on the types of sensing desired. For instance, certain types of physiological parameters may be advantageously sensed using an implantable device and other may be more advantageously sensed with a wearable device.

The medical device system 200 can include an external communication device 212 to communicate with the ambulatory medical device. The communication may be wireless using wireless telemetry. The external communication device 212 may communicate with a remote system 214 via a network 218 (e.g., the internet, a proprietary computer network, or a cellular phone network). The remote system 214 may include a server 216 remotely located from the external communication device 212 and the HF subject to perform patient management functions, such as accessing electronic medical records for example. The external communication device 212 may include a programmer to program therapy parameters of a device-based therapy provided by the ambulatory device. In certain examples, the external communication device 212 includes a repeater to communicate programming changes or other communication initiated by the remote system 214. The term repeater refers to a communication device local to the patient to relay communication signals between the remote system 214 and the medical device system 200.

Figure 3:
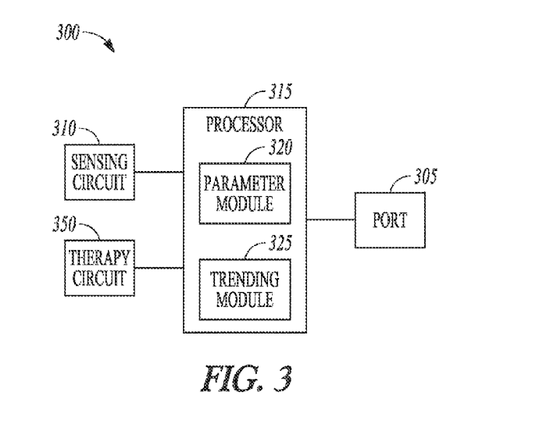
FIG. 3 shows portions of another example of a medical device system for monitoring effects of dosing of a heart failure subject.

FIG. 3 shows a block diagram of an example of portions of a medical device system 300. The system includes a port 305 to receive an indication of dosing of medication to treat a pulmonary condition of the HF subject. The port 305 may be electrically coupled to a communication circuit (not shown). The communication circuit may communicate wireless signals with a separate device and the port 305 may receive the indication as a wireless signal. The port 305 may be electrically coupled to a user interface if the device is wearable and the port 305 may receive the indication from a user. The indication may be of dosing of medication to treat COPD. The indication may be of dosing of the HF subject with a cortico-steroid.

The system includes at least one sensing circuit 310 and at least one processor 315. The sensing circuit 310 senses at least one physiological signal that includes physiological information of the HF subject. The processor 315 may be a microprocessor, a digital signal processor, application specific integrated circuit (ASIC), or other type of processor, interpreting or executing instructions in software modules or firmware modules. The modules may include software, firmware, hardware circuits or any combination of software, firmware, and hardware. Multiple functions can be performed in one or more of the modules as desired.

The system can be included in an ambulatory device such as the examples shown in FIG. 2, and the processor 315 can include a parameter module 320 and a trending module 325. The parameter module 320 extracts values of at least one physiological parameter indicative of health status of the HF subject using the sensed physiological signal. The trending module 325 trends extracted values of the physiological parameter and detects an effect of the dosing of the medication on the HF subject using the trending of the extracted values of the at least one physiological parameter. The detected effect can be one or both of a side effect of the dosing and the effectiveness of the dosing.

To determine effectiveness of the dosing, respiration can be monitored. For instance, the sensing circuit 310 can include a respiration sensing circuit that senses a respiration signal that includes respiration information of the HF subject. Some examples of the respiration sensing circuit include a motion sensing circuit (e.g., an accelerometer) that senses motion of the thoracic cavity of the subject, and a thoracic impedance sensing circuit. For thoracic impedance, electrodes may be placed across at least a portion of the thorax region of the subject to obtain a signal of thoracic impedance which changes in time with respiration. An approach to measuring thoracic impedance is described in Hartley et al., U.S. Pat. No. 6,076,015 "Rate Adaptive Cardiac Rhythm Management Device Using Transthoracic Impedance," filed Feb. 27, 1998, which is incorporated herein by reference in its entirety.

The parameter module 320 extracts a value of a respiration parameter of the HF subject using the respiration signal. Some examples of a respiration parameter include a respiration rate, an inter-breath interval, a measure of variability of respiration rate, a measure of variability of an inter-breath interval, the tidal volume, a measure of variability of tidal volume of the HF subject, end-expiratory volume (EEV), minute ventilation, or a rapid shallow breathing index (RSBI).

The trending module 325 trends values of the respiration parameter and generates an indication of effectiveness of the dosing of the medication using the trend of values of the respiration parameter. For example, the trending module 325 may generate an indication that the treatment is effective when the respiration rate of the HF subject decreases to satisfy a specified (e.g., programmed) respiration rate threshold. The trending module 325 may generate an indication that the treatment is effective when the respiration rate of the HF subject falls into a specified respiration rate range. The trending module 325 may generate an indication that the treatment is effective when the respiration parameter satisfies a specified threshold within a specified period of time, such as measured from the time of the dosing or when the dosing indication was received for example.

In another example, effectiveness of the dosing can be determined by monitoring lung tissue inflammation. Sensing one or more of lung impedance, blood gas, and exhaled breath gas can provide a surrogate measurement of lung inflammation.

In some examples, the sensing circuit 310 includes at least one of a lung impedance sensing circuit, a blood gas sensing circuit, and an exhaled breath gas sensing circuit. For the lung impedance sensing circuit, a thoracic impedance signal may include a higher frequency signal component that changes in time with respiration and a lower frequency component that changes with the condition of the HF subject's lungs, such as due to lung tissue inflammation. The trending module 325 may trend values of the lower frequency component of the impedance signal and generate an indication of effectiveness of the dosing of the medication on the HF subject using the trend of impedance values.

Sensing blood gas can provide a measure of oxygen ($O_2$) or carbon dioxide ($CO_2$). The blood gas sensing circuit can include an implantable oxygen saturation sensor. An oxygen saturation sensor produces an electrical sensor signal associated with changes in the fluid oxygen concentration, such as hemoglobin oxygen saturation for example. The fluid oxygen may change due to lung tissue inflammation. The trending module 325 may trend values of oxygen saturation level and generate an indication of effectiveness of the dosing of the medication on the HF subject using the trend of oxygen saturation levels. Sensing exhaled breath gas can provide measure of oxygen, carbon dioxide, or an inflammatory indicator such as nitric oxide (NO). The exhaled breath gas sensing circuit can include a chemical sensor to detect one or more of oxygen, carbon dioxide, or nitric oxide.

In another example, effectiveness of the dosing can be determined by monitoring airway function. For instance, a pressure sensor could be arranged in the pleural space. The ratio of the respiratory swings in that pressure to tidal volume would be an approximate index of airway function. The sensing circuit may include a spirometer to monitor lung capacity or forced expiratory volume (FEV1). Spirometric values could be monitored after the dosing.

In addition to, or in the alternative, to determining effectiveness of the dosing of the medication, the system 300 may monitor one or more physiological parameters to detect side effects from the dosing. A non-exhaustive list of such physiological parameters includes heart rate, blood pressure, heart contractility, arrhythmia burden, thoracic impedance, and a parameter related to heart sounds.

In some examples, the sensing circuit 310 includes a cardiac signal sensing circuit and the physiological signal includes a cardiac activity signal representative of electrical cardiac activity of the subject. The cardiac activity signal can be used to monitor one or more of heart rate, heart contractility, and arrhythmia burden. For instance, heart rate can be monitored by the parameter module 320 tracking intervals between a fiducial in the cardiac activity signal such as an R-wave. An R-wave is part of the QRS complex in an electrogram signal or electrocardiogram signal that represents ventricular depolarization. Heart contractility may be monitored by the parameter module 320 measuring the width of the QRS complex. In some examples, the processor includes an arrhythmia detection module (not shown). The arrhythmia detection module detects cardiac arrhythmia (e.g., atrial tachyarrhythmia and ventricular tachyarrhythmia), such as by using one or more of heart rate and signal morphology analysis for example. The parameter module 320 may determine arrhythmia burden according to the detected cardiac arrhythmia. The trending module 325 may trend values of at least one of heart rate, heart contractility, or arrhythmia burden to detect a side effect of the dosing, such as increased heart rate, a decrease in cardiac contractility, or an increase in arrhythmia burden.

In some examples, the sensing circuit 310 includes a heart sound signal sensing circuit and the physiological signal includes a heart sound signal. Some examples of a heart sound signal sensing circuit include an accelerometer and a microphone. The parameter module 320 may extract a heart sound parameter using the heart sound signal. A non-exhaustive list of examples of heart sound parameters includes the amplitude of a heart sound (e.g., the S1 heart sound), the duration of a heart sound, and a time interval between heart sounds. In some examples, the device includes both a cardiac signal sensing circuit and a heart sound signal sensing circuit. The parameter module 320 may extract an interval between a fiducial in the cardiac activity signal and a fiducial in the heart sound signal as the heart sound parameter. In some examples, the parameter module 320 extracts a measure of heart contractility using the heart sound parameter. The trending module 325 may trend values of the heart sound parameter to detect a side effect of the dosing, such as an increase in the amplitude of the S1 that may indicate higher contractility, or an increase in amplitude of the S3 heart sound that may indicate fluid retention.

In some examples, the sensing circuit 310 provides blood pressure signal to monitor blood pressure of the HF subject. The trending module 325 may trend values of blood pressure to detect an increase in blood pressure as a side effect of the dosing. Monitoring thoracic impedance can also be useful to detect a side effect of the dosing. The trending module 325 may trend values of the heart sound parameter to detect a side effect of the dosing, such as fluid retention in the lungs of the HF subject.

The trending module 325 may detect the side effect of the dosing of the medication on the HF subject when detecting that a value of the physiological parameter exceeds a specified threshold value of the at least one physiological parameter or falls outside of a specified range of values for the parameter. In certain examples, the trending module 325 detects the side effect when detecting that a change in value of the physiological parameter exceeds a specified threshold change value within a specified time duration. The time duration can be measured from the time when the indication of the dosing is received. In certain examples, the trending module 325 determines an integral of the values of physiological parameter. The trending module 325 may determine the integral using a summation, or by calculating the area under a waveform corresponding to the physiological signal. If the side effect is sustained, the value of the integral will be increasing. The trending module detects the side effect when detecting that the integral of values of the physiological parameter exceeds a specified threshold integral value of the physiological parameter.

In some examples, the system 300 includes a therapy circuit 350 to control delivery of drug therapy to the HF subject. The processor 315 may initiate at least one of delivery of drug therapy or a change in a parameter of the drug therapy in response to detection of the effect of the dosing of the medication on the HF subject. In some examples, the therapy circuit 350 provides electrical cardiac therapy to the HF subject. The processor 315 initiates at least one of the electrical cardiac therapy or a change in a parameter of the electrical cardiac therapy in response to detection of a side effect of the dosing of the medication on the HF subject. In some examples, therapy is triggered by a command sent from a separate device by a user, such as in response to an alert generated by the system.

The system 300 may include one or any combination of the sensing circuits described herein. One or more of the sensing circuits can be included to monitor effectiveness of the dosing and one or more of the sensing circuit can be included to detect a side effect of the dosing. One or more of the sensing circuits can be included in a device separate from the device with the processor 315. For example the system 300 can a first implantable medical device and a second ambulatory medical device. The implantable device can include the sensing circuit 310 and a communication circuit to communicate information with the ambulatory device. The ambulatory medical device can include the processor 315 having the parameter module 320, the trending module 325, and a communication circuit to communicate information with the implantable medical device. The ambulatory medical device may also include one or more sensing circuits.

Figure 4:
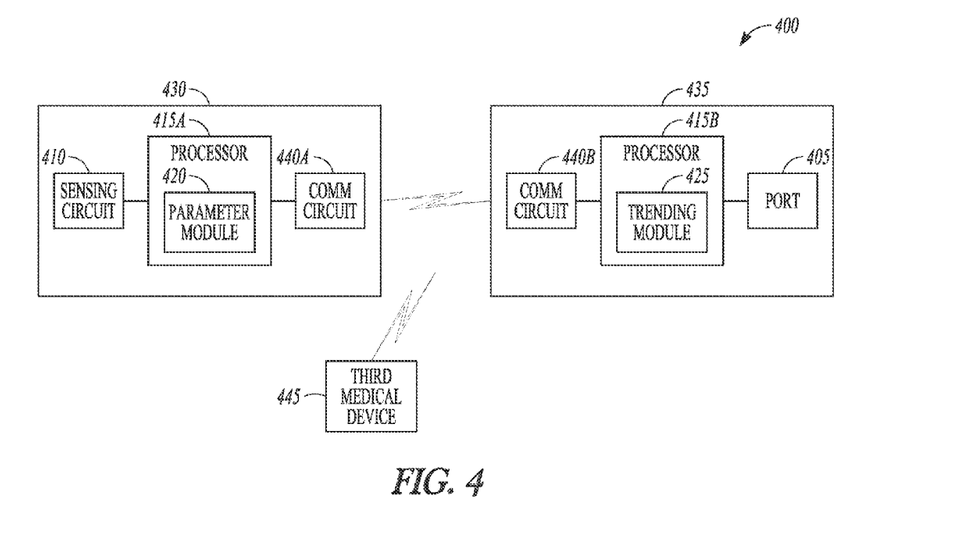
FIG. 4 shows portions of still another example of a medical device system for monitoring effects of dosing of a heart failure subject.

Other architectures are possible and the device elements in FIG. 3 may be arranged with multiple processors with the functions of the parameter module and trending module divided between the processors. FIG. 4 shows portions of an example of a medical device system 400. The system 400 includes a first ambulatory medical device 430 and a second medical device 435. The second medical device 435 may be located remotely from the ambulatory medical device 430. The ambulatory medical device 430 includes a sensing circuit 410, a first processor 415A that includes the parameter module 420, and a communication circuit 440A configured to communicate information with the second medical device 435. The communication can be wireless such as by wireless inductive telemetry or far field radio frequency communications. The second medical device 435 includes a second processor 415B that includes the trending module 425 and a communication circuit 440B configured to communicate information with the ambulatory medical device 430. In some examples, the parameter module 420 extracts a physiological parameter from a physiological signal sensed by the sensing circuit and communicates physiological parameters to the second medical device 435 for trending. The second medical device 435 may include the port 405 to receive the indication of dosing of the medication.

The system 400 can include a third medical device 445 having communication circuit for communication with the second medical device 435. The communication between the second and third medical devices may be wired or wireless and the communication may occur over a network. The third medical device 445 may provide a physiological parameter of the HF subject to the second medical device 435 for trending. For example, the third medical device may include a blood pressure cuff and communicate values of blood pressure of the HF subject to the second medical device 435 for trending. The trending module 425 may trend values of blood pressure and values of the physiological parameter received from the ambulatory device 430 to determine one or both of effectiveness of the dosing and a side effect of the dosing.

In some examples the third medical device 445 includes a spirometer and the third medical device 445 communicates a measurement of one or more of lung capacity and forced expiratory volume (FEV1) to the second medical device 435. The trending module 425 may trend values of the measurement by the spirometer and values of the physiological parameter from the ambulatory medical device 430 to determine one or both of effectiveness of the dosing and a side effect of the dosing. The third medical device may also include an exhaled gas sensing circuit (e.g., a handheld device) that measure nitric oxide or other breath gas inflammatory marker or indicator.

Figure 5:
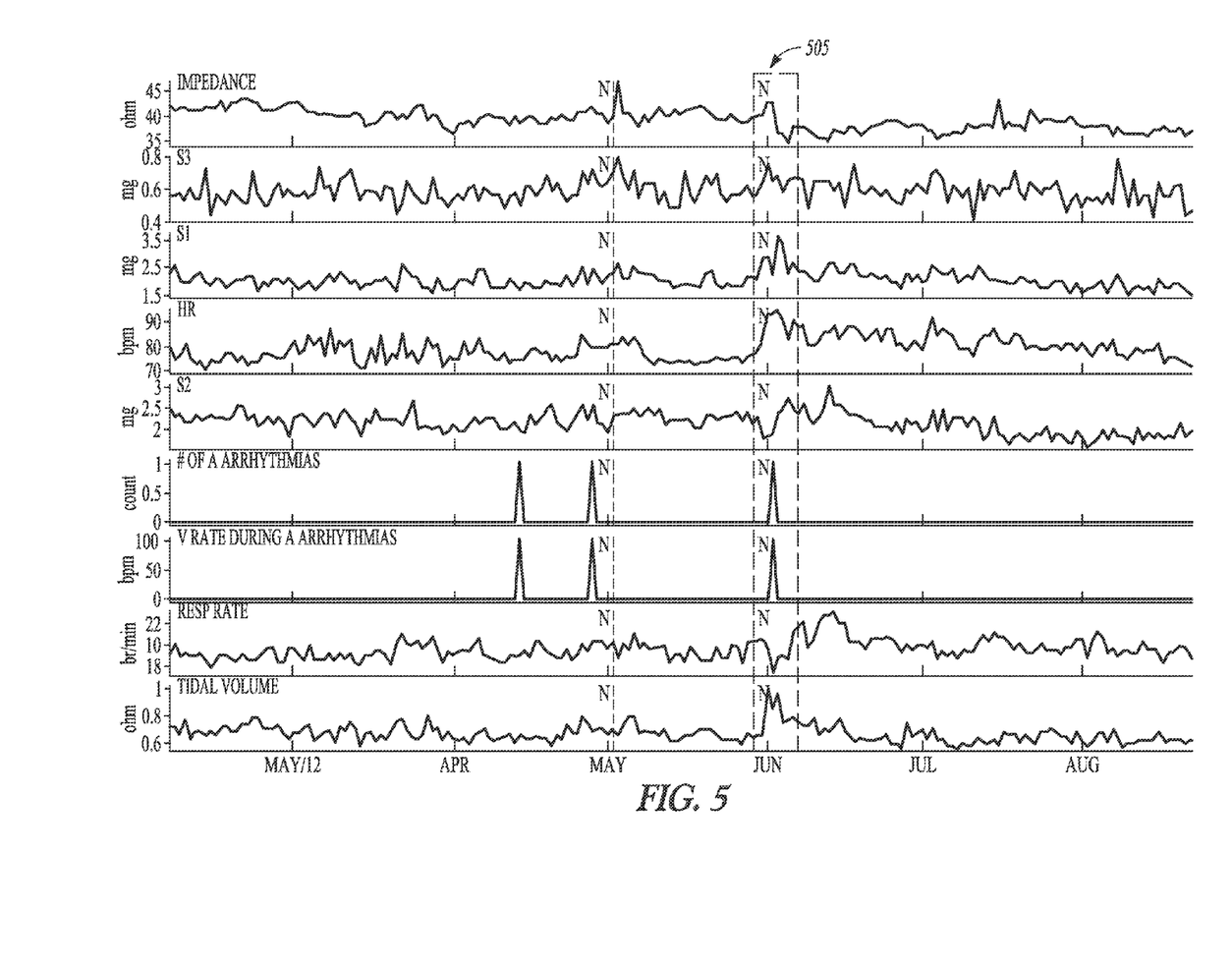
FIG. 5 shows an example of waveforms of physiological parameters.

FIG. 5 shows an example of waveforms of physiological parameters versus time. The parameters were sensed from an HF subject and include thoracic impedance, the amplitude of the S3 heart sound, the amplitude of the S1 heart sound, heart rate (HR), the amplitude of the S2 heart sound, arrhythmia burden, arrhythmia ventricular depolarization rate, respiratory rate (RR), and tidal volume (TV).

The right-most vertical dashed line 505 indicates an episode when the HF subject experienced an exacerbation of COPD and was hospitalized. The HF subject was treated with corticosteroids intravenously at the beginning of the episode and prescribed oral corticosteroids after being discharged. Worsening of HF of the subject can be detected by sensing one or both of sensing thoracic impedance (e.g., to monitor congestion and hyperinflation breathing patterns due to COPD) and the amplitude of the S3 heart sound (e.g., to monitor elevated filling pressure due to HF).

Effectiveness of the dosing of the corticosteroids can be determined by, among other things, monitoring one or any combination of thoracic impedance, the amplitude of the S3 heart sound, the respiratory rate, and tidal volume. Side effects of the corticosteroids can include increased heart contractility (detected by monitoring S1), increased heart rate, and increased arrhythmias (detected by monitoring one or both of arrhythmia burden and ventricular rate during arrhythmia).

For the portions of the waveforms following the vertical dashed line 505, the parameters show a decrease in respiratory rate, an increase in tidal volume, and a decrease in thoracic impedance; indicating effectiveness of the medication and resolution of the hyperinflation breathing patterns. For a segment of a week or two shown by the dashed lines 505, the parameters show an elevation in heart rate and in the amplitude of S1 and S2; reflecting side effects of the corticosteroids.

An indication of effectiveness of the dosing or of a side effect of the dosing can be generated by the medical system. The indication can be provided to a user or process. For instance, the second medical device 435 of FIG. 4 may recommend a change to the dosing based on the indication. An indication of a side effect can be an alert sent to at least one of a user or process. One or more clinicians, care givers, and patients can be notified when a side effect condition is detected.

Device-based monitoring of the effectiveness and side effects of medication prescribed to treat pulmonary conditions of HF patients can result in the best dosage prescribed for the individual patient; leading to minimization of discomfort for the patient.

ADDITIONAL NOTES

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A system comprising:
   a port configured to receive an indication of dosing of medication to treat a pulmonary condition of a heart failure (HF) subject;
   at least one sensing circuit configured to sense at least one physiological signal, wherein the physiological signal includes physiological information of the HF subject;
   at least one processor including:
      a parameter module configured to extract values of at least one physiological parameter indicative of health status of the HF subject; and
      a trending module configured to trend extracted values of the at least one physiological parameter, to detect a side effect of the dosing of the medication on the HF subject when detecting that a value of the physiological parameter exceeds a specified threshold value of the at least one physiological parameter, and to output an indication of the detected side effect of dosing; and
   an alert unit configured to notify the detected side effect of dosing to a user.

2. The system of claim 1, wherein the sensing circuit includes a respiration sensing circuit configured to sense a respiration signal that includes respiration information of the HF subject,
   wherein the parameter module is configured to extract a value of a respiration parameter of the HF subject using the respiration signal, and
   wherein the trending module is configured to trend values of the respiration parameter and generate an indication of effectiveness of the dosing of the medication on the HF subject using the trend of values of the respiration parameter.

3. The system of claim 1, wherein the at least one physiological signal includes at least one of a cardiac activity signal, a thoracic impedance signal, a heart sound signal, and a blood pressure signal, and
   wherein the parameter module is configured to extract values of at least one of heart rate, heart contractility, arrhythmia burden, thoracic impedance, at least one heart sound parameter, and blood pressure from the at least one physiological signal, and
   wherein the trending module is configured to trend values of at least one of heart rate, heart contractility, arrhythmia burden, thoracic impedance, at least one heart sound parameter, and blood pressure, and detect a side effect of the dosing of the medication on the HF subject using the trending.

4. The system of claim 1, wherein the at least one physiological signal includes thoracic impedance information of the HF subject, wherein the parameter module configured to extract values of thoracic impedance from the physiological signal, and wherein the trending module is configured to trend values of thoracic impedance and generate an indication of effectiveness of the dosing of the medication on the HF subject using the trend of the measure of thoracic impedance.

5. The system of claim 1, wherein the trending module is configured to detect a side effect of the dosing of the medication on the HF subject when detecting that a value of the integral of values of the physiological parameter exceeds a specified threshold integral value of the at least one physiological parameter.

6. The system of claim 1, wherein the system includes a first ambulatory medical device and a second medical device, wherein the ambulatory medical device includes a first processor that includes the parameter module and a communication circuit configured to communicate information with the second device, wherein the second device includes a second processor that includes the trending module and a communication circuit configured to communicate information with the ambulatory device.

7. The system of claim 6, including a third medical device that includes a spirometer and a communication circuit configured to communicate information with the second device, wherein the third medical device is configured to communicate a measurement of one or more of lung capacity and forced expiratory volume (FEV1) to the second device, and wherein the trending module is configured to trend values of the at least one physiological parameter and values of the measurement by the spirometer and detect the side effect of the dosing of the medication on the HF subject using the trending.

8. The system of claim 6, including a third medical device that includes an exhaled gas sensing circuit and a communication circuit configured to communicate information with the second device, wherein the third medical device is configured to communicate a measurement of a breath gas inflammatory indicator to the second device, and wherein the trending module is configured to trend values of the at least one physiological parameter and values of the measurement by the exhaled gas sensing and detect the side effect of the dosing of the medication on the HF subject using the trending.

9. The system of claim 1, wherein the system includes a first implantable medical device and a second ambulatory medical device, wherein the implantable device includes the sensing circuit and a communication circuit configured to communicate information with the ambulatory device, and wherein the ambulatory medical device includes the processor having the parameter module and the trending module and includes a communication circuit configured to communicate information with the implantable medical device.

10. The system of claim 1, including a therapy circuit configured to control delivery of drug therapy to the HF subject, and wherein the at least one processor is configured to initiate at least one of delivery of drug therapy or a change in a parameter of the drug therapy in response to detection of the effect of the dosing of the medication on the HF subject.

11. The system of claim 1, including a therapy circuit configured to provide electrical cardiac therapy to the HF subject, wherein the at least one processor is configured to initiate at least one of the electrical cardiac therapy or a change in a parameter of the electrical cardiac therapy in response to detection of the effect of the dosing of the medication on the HF subject.

12. The system of claim 1, wherein the sensing circuit includes at least one of an impedance sensing circuit, a blood gas sensing circuit or breath gas sensing circuit, and the physiological signal includes information of at least one of thoracic impedance or blood oxygen saturation level, wherein the parameter module is configured to extract a value of at least one of thoracic impedance or blood oxygen level, and wherein the trending module is configured to trend values of at least one of thoracic impedance or blood oxygen level and generate an indication of effectiveness of the dosing of the medication on the HF subject using the trend of values.

13. A method of operating a medical device, the method comprising:
  receiving, into the medical device, an indication of dosing of medication to treat a pulmonary condition of a heart failure (HF) subject;
  sensing at least one physiological parameter indicative of health status of the HF subject using the medical device and trending values of the at least one physiological parameter; and
  detecting, using a processor, a side effect of the dosing of the medication on the HF subject when a value of the physiological parameter exceeds a specified threshold value of the at least one physiological parameter; and
  providing an indication, using an alert unit, of the effect to a user.

14. The method of claim 13, wherein detecting an effect of the dosing of the medication on the HF subject includes at least one of detecting a side effect of the dosing or detecting effectiveness of the dosing.

15. The method of claim 13,
  wherein sensing the at least one physiological parameter includes sensing a respiration parameter of the HF subject, and
  wherein the method includes trending values of the respiration parameter and generating an indication of effectiveness of the dosing of the medication on the HF subject using the trend of the respiration parameter.

16. The method of claim 15, wherein sensing at least one physiological parameter includes sensing at least one of heart rate of the HF subject, heart contractility of the HF subject, arrhythmia burden of the HF subject, thoracic impedance of the HF subject, amplitude of at least one heart sound of the HF subject, and blood pressure of the HF subject, and
  wherein trending values of the at least one physiological parameter includes trending at least one of heart rate, heart contractility, arrhythmia burden, intra-thoracic impedance, heart sound amplitude, or blood pressure, and detecting a side effect of the dosing using the trending.

17. The method of claim 13, wherein the at least one physiological parameter includes a measure of thoracic impedance, and wherein the method further includes generating an indication of effectiveness of the dosing of the medication on the HF subject using the trend of the measure of thoracic impedance.

18. A system comprising:
  a port configured to receive an indication of dosing of medication to treat a pulmonary condition of a heart failure (HF) subject;
  at least one sensing circuit configured to sense at least one physiological signal wherein the physiological signal includes physiological information of the HF subject;
  at least one processor including:
    a parameter module configured to extract values of at least one physiological parameter indicative of health status of the HF subject; and
    a trending module configured to trend extracted values of the at least one physiological parameter, to detect a side effect of the dosing of the medication on the HF subject when detecting that a change in value of the physiological parameter exceeds a specified threshold change value of the at least one physiological parameter within a specified time duration, and to output an indication of the detected side effect of dosing; and a therapy circuit to control therapy to the HF subject based on the indication of the detected side effect of dosing.

\* \* \* \* \*